United States Patent [19]
Campopiano et al.

[11] Patent Number: 6,001,097
[45] Date of Patent: *Dec. 14, 1999

[54] FRACTURE REDUCING APPARATUS

[75] Inventors: Ascanio Campopiano, Torre del Greco, Italy; Jacques Mata, Etoy, Switzerland

[73] Assignee: Jaquet Orthopedie S.A., Switzerland

[ * ] Notice: This patent issued on a continued prosecution application filed under 37 CFR 1.53(d), and is subject to the twenty year patent term provisions of 35 U.S.C. 154(a)(2).

[21] Appl. No.: 08/781,399

[22] Filed: Jan. 10, 1997

[30] Foreign Application Priority Data

Jan. 18, 1996 [CH] Switzerland ................. 133/96

[51] Int. Cl.$^6$ .................................................. A61B 17/56
[52] U.S. Cl. ................. 606/57; 606/54; 606/102
[58] Field of Search ................. 606/54–58, 102

[56] References Cited

U.S. PATENT DOCUMENTS 2,391,537  12/1945  Anderson ................. 128/84
4,620,533  11/1986  Mears ................. 128/92
5,397,322   3/1995  Campopiano ................. 606/57

FOREIGN PATENT DOCUMENTS 177270      4/1986  European Pat. Off. .
WO 92/02184 2/1992  WIPO .

Primary Examiner—Michael Buiz
Assistant Examiner—Julian W. Woo
Attorney, Agent, or Firm—Lerner, David, Littenberg, Krumholz & Mentlik, LLP

[57] ABSTRACT

A reducing apparatus allows each displacement which has been effected to be analyzed and precisely measured. It includes three telescopic bars disposed along the axes x, y and z, respectively, of an orthonormal system, and connected to one another by joining pieces which are movable in relation to the telescopic bars. An angled arm is provided whose ends are formed by two pivoting discs which are disposed in perpendicular planes, these discs permitting the rotation about the axes y and z. Also provided is an adjustable circular sector made up of an arc and a mobile carriage which are intended to effect the rotations about the axis x.

16 Claims, 3 Drawing Sheets

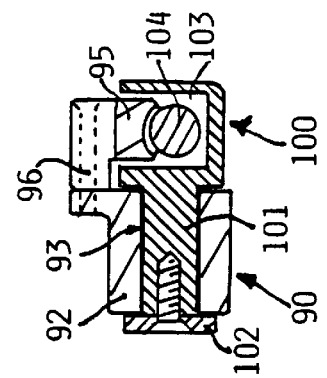
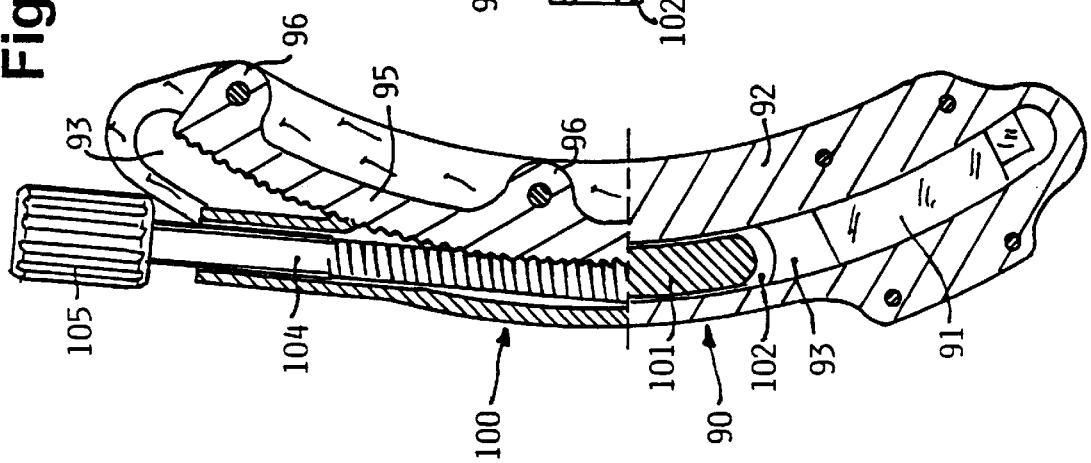
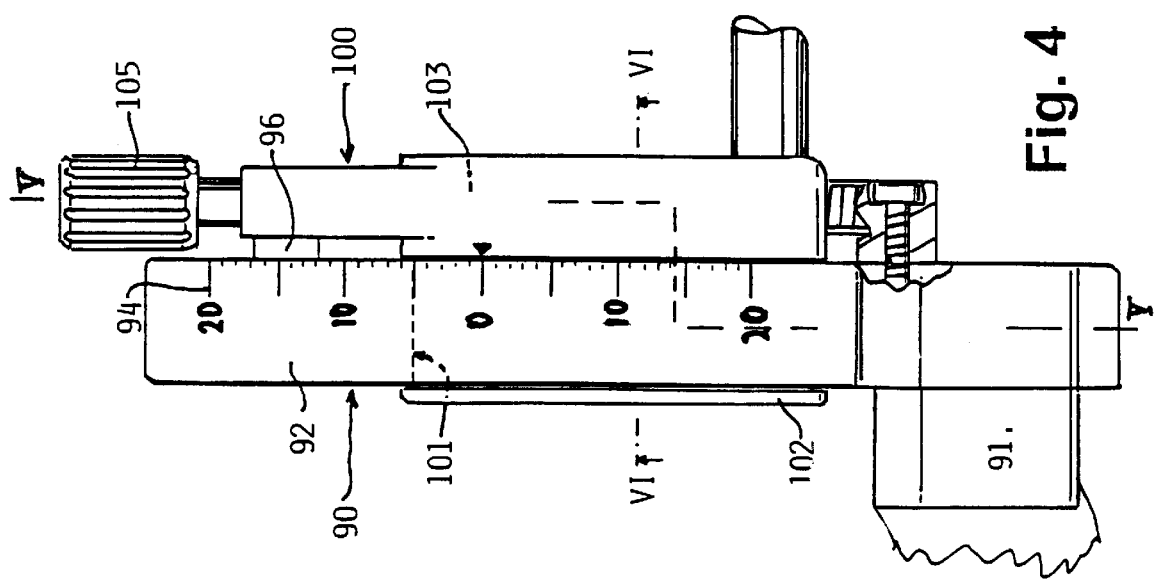

6,001,097

FRACTURE REDUCING APPARATUS

BACKGROUND OF THE INVENTION

1. Field of the Invention

The present invention concerns the field of fracture fixation and relates more particularly to an apparatus which is used in the external fixation of fractured bones.

2. Description of the Prior Art

A large number of external fixators are known which are connected to the bone fragments by sets of pins which are inserted into each of the bone fragments. The problem involved in putting this type of fixator into place is that of being able to return the bone fragments to the precise original position. Thus, fixators have already been proposed with which it is possible to orient the pins, and consequently the bone fragments. U.S. Pat. No. 5,160,335, for example, describes a fixator which includes two supports for bone pins which supports are separated by a telescopic bar. It is possible for each support to be pivoted in three orthonormal axes.

U.S. Pat. No. 5,397,322 discloses a reducing apparatus arranged between two clamps for gripping the pins which are inserted in each of the bone fragments. This reducing apparatus includes an adjustable circular sector which is equipped at each end with means for rotation and axial displacement of one of the gripping clamps. It thus permits a micrometric displacement of the bone fragments in all degrees of freedom, by means of axial displacements and angular rotations. The manipulations can thus be performed independently of one another in such a way as not to compromise a reduction result which has already been achieved. The teachings of U.S. Pat. No. 5,397,322 are incorporated herein by reference.

However, the design of these prior art devices makes it difficult for the practitioner to visualize the movement he will effect using one of the numerous screws or adjustment levers. In seeking to improve the relative positioning of the bone fragments, one runs the risk of disturbing the results which have already been obtained.

SUMMARY OF THE INVENTION

The object of the present invention is to remedy the drawbacks in the prior art devices by proposing a fracture reducing apparatus with which it is possible to visualize precisely the displacement generated by actuating one of the adjustment elements. The subject of the present invention is a reducing apparatus which includes an adjustable circular sector, means for linear displacements and means for angular rotations, the circular sector being divided into two arc-shaped parts which slide in relation to each other. Each of the arc-shaped parts is coupled to pins which are inserted in each of the fractured bone fragments. This device has an angled arm whose ends include two pivoting discs one of the discs cooperating with the means for linear displacements, and the other disc cooperating with the adjustable circular sector. This reducing apparatus thus makes it possible to execute translational movements which are physically distinct from the rotational movements.

The manipulator of the present invention will preferably be used during the reduction of the fracture and will permit positioning of an external fixator after which it is removed. The manipulator can also be left in place, especially if the intention is to proceed subsequently with other manipulations.

The invention also extends to a method for putting this reducing apparatus into place, characterized in that the reducing apparatus is disposed in a position such that the angled arm is situated in a plane perpendicular to the fractured bone, and that the axis of the circular sector is on the site of the fracture. The means for linear displacement is situated on one side of this plane, while the means of rotation is disposed on the other side, just as the bone fragments are distributed on either side of this plane.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views:

FIG. 4 is a front view of the double arc-shaped sector of the manipulator in FIG. 1;

FIG. 5 is a longitudinal section of the components of the double sector, along the broken line V—V in FIG. 4; and FIG. 6 is a transverse section along the line VI—VI in FIG. 4.

DESCRIPTION OF THE PREFERRED EMBODIMENT

Figure 1:
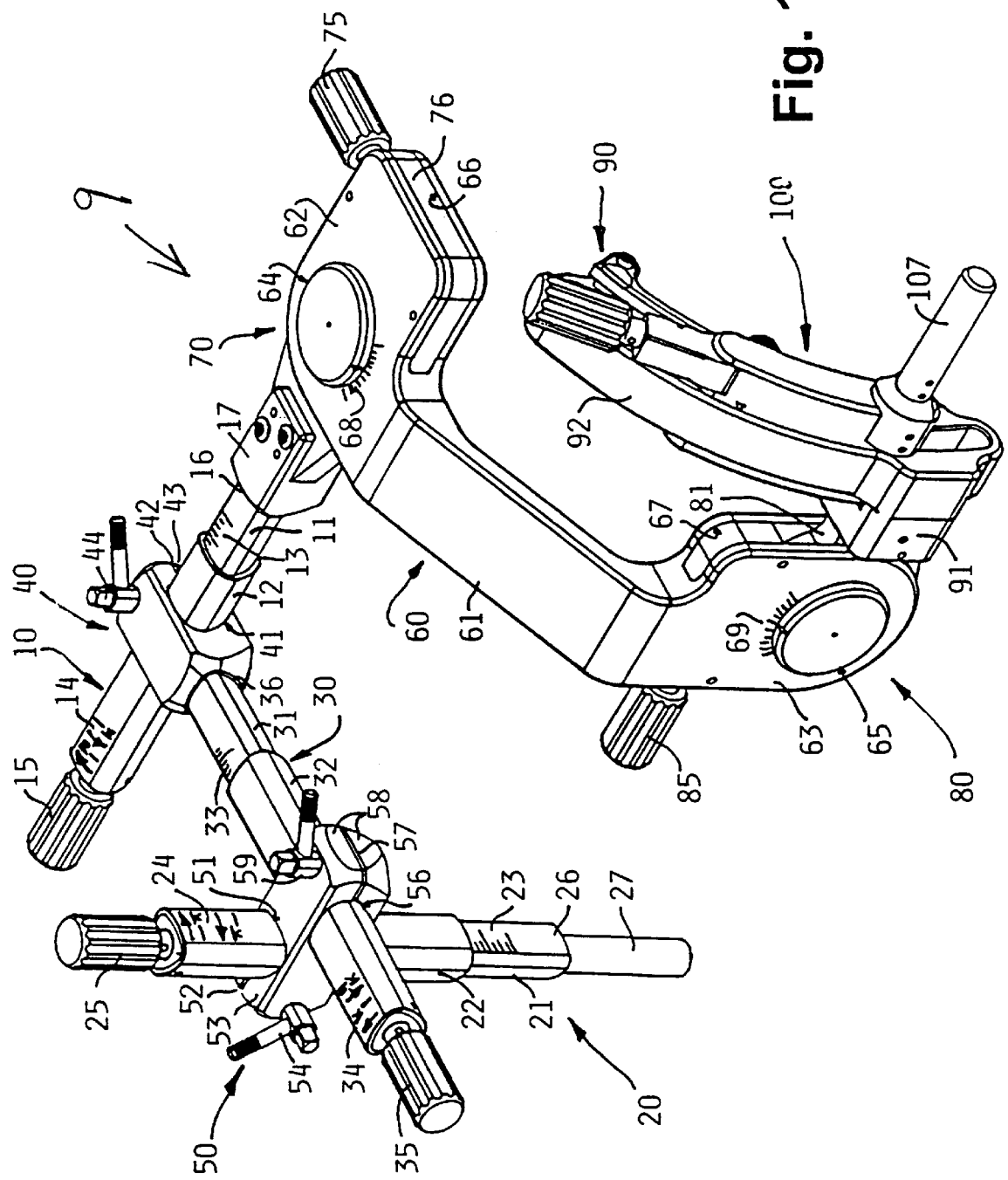
FIG. 1 is a perspective view of a manipulator according to the invention.

Referring to the apparatus represented in FIG. 1 generally denoted as 9, it includes three telescopic bars 10, 20, 30 disposed along the axes x, y and z, respectively, of an orthonormal system. These telescopic bars are connected to one another by joining pieces 40 and 50 which are moveable in relation to the telescopic bars so as to permit rough adjustment of the positioning of the assembly in relation to the fractured limb, so that the patient is not inconvenienced.

Figure 2:
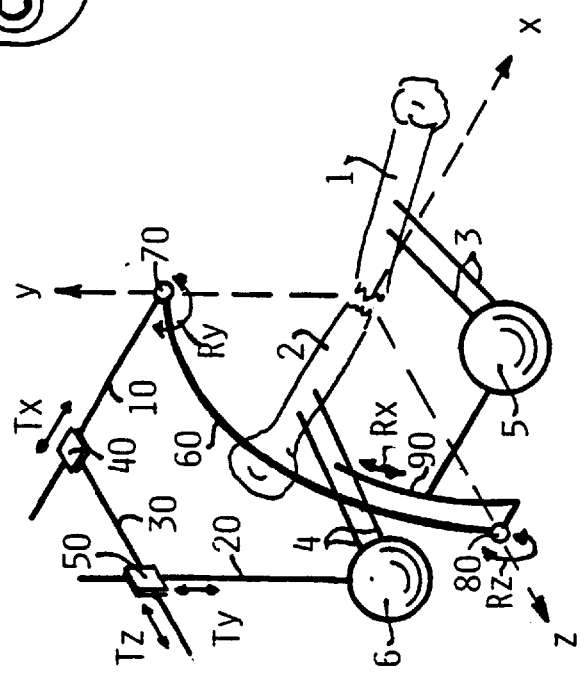
FIG. 2 is an outline diagram of the manipulator in FIG. 1, representing its positioning in relation to a bone, the fragments of which are held in place by bone pins.

One end of bar 10 is connected to the components of the manipulator with which it is possible to effect rotational movement. For this purpose, the manipulator includes an angled arm 60 whose ends are formed by two pivoting discs 70 and 80 which are disposed in perpendicular planes, these discs permit rotation about the axes y and z. As shown in FIG. 1 and FIG. 2, disc 70 is connected to telescopic bar 10, and disc 80 is connected to a curved element 90 intended to effect the rotations about the axis x.

The various movements described hereinabove are shown in detail in the diagram in FIG. 2, where the arrows Tx, Ty and Tz represent the translational movements along the axes x, y, and z, respectively, while the arrows Rx, Ry and Rz represent the possibilities of rotation about these axes.

FIG. 2 also shows two fragments 1 and 2 of a long bone, the sets of bone pins 3 and 4 inserted in the fragments 1 and 2 and held in place in vices 5 and 6, symbolized in this diagram by balls which are integral, respectively, with the mobile carriage of curved element 90 and with one end of the attachment bar 20.

It should be noted that the manipulator of FIG. 2 is disposed in such a way that the bone fragment 2 is substantially on the axis x, its fractured end being positioned at the point of origin of the system of orthonormal coordinates x, y and z. It will also be noted in this diagram that the transverse bars are to the left of the plane (y, z), whereas all the components with which it is possible to effect the rotations are disposed to the right of the said plane, just as the bone fragments are distributed on either side of the plane (y, z).

Referring to FIG. 1, it will be noted that telescopic bars 10, 20 and 30 each include an inner tube 11, 21, 31 and an outer tube 12, 22, 32. In the embodiment shown in FIG. 1, these tubes have a generally triangular cross-section in order to prevent any rotation of the components in relation to one another. Inner tubes 11, 21, 31 include a millimetric scale 13, 23, 33 formed thereon representing displacements of a few centimeters on either side of a zero point. The outer tubes have arrow indications 14, 24, 34 with which it is possible to visualized the displacement obtained in the direction of rotation of the knobs 15, 25, 35 disposed at one of the ends of the outer tubes 12, 22, 32. These knobs 15, 25, 35 are made integral, in a known manner, with an endless screw cooperating with the inner tubes of the telescopic bars.

The free end 16 of inner tube 11 is fixed to a grip 17 for connection to the components of rotations of the manipulator. The end 26 of tube 21 is integral with a bar 27 for fixing of the pin-holder flange shown schematically by the ball 6 as shown in FIG. 2. As for the free end 36 of tube 31, it is fixed in the connecting element 40.

Connecting element 40 is intended to slide along the outer tube 12. It therefore has an opening 41 of a shape corresponding to the outer shape of tube 12. This opening includes a slot 42 thereby forming two jaws 43 which are intended to be brought together by means of clamp 44. Slot 42 in element 40 is elastically compressed by clamp 44 thereby locking element 40 on tube 12. Likewise, connecting element 50 is intended for the relative movement of the telescopic bars 20 and 30. It thus includes two openings 51 and 56 with a shape corresponding to the outer shape of tubes 22 and 32. These openings include slots 52 and 57 which form two jaws 53 and 58 which are intended to be brought together by means of clamps 54 and 59 in a similar fashion as described above for clamp 44.

As has already been mentioned, angled arm 60 is centered on the fracture. It is made of a radiolucent material, for example carbon fiber. It consists of a central part 61 between two plates 62 and 63 which are disposed in perpendicular planes and which are intended to receive pivoting discs 70 and 80. The plates 62, 63 each include a passage 64, 65 of a round shape, and an opening 66, 67 which opens to the outside and which is intended to receive the rotation controls. The angle of rotation can be set using the scales 68 and 69, which preferably are graduated from −20° to +20°.

Figure 3:
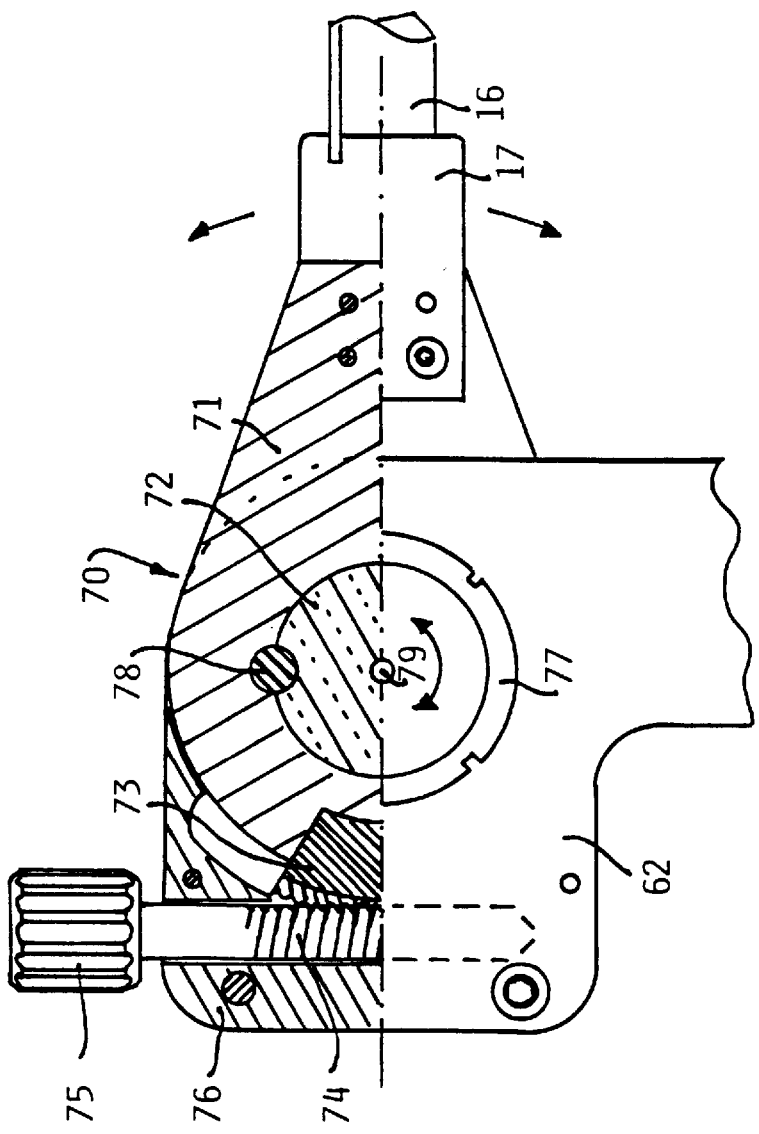
FIG. 3 is a bottom view of the horizontal rotation plate of the manipulator in FIG. 1, with longitudinal sectioning of the components situated in the upper half of the drawing.

Referring to FIG. 3 representing pivoting disc 70, end 16 of the telescopic tube is again shown. End 16 is fixed in the grip 17 which is made integral with an arm 71 integral with a shaft 72. Arm 71 and central shaft 72 and preferably radiolucent. Arm 71 includes a toothed sector 73 which is intended to cooperate with a screw 74 driven by a knob 75. These different components are held in place in the inner opening 66 of plate 62 by a central body 76 which is held on plate 62 by screws and which has an opening for the toothed sector 73 and a passage fro the screw 74. The unthreaded ends of screw 74 turn in bearings or bushings (not shown). Central shaft 72 includes, on either side of plate 62, a collar 77 which is intended to hold the shaft in place during its pivoting in passage 64 formed in plate 62. Central shaft 72 is moreover made integral with arm 71 by way of a small pin 78 to ensure pivoting in the direction of the arrows when knob 75 is acted upon. Finally, central shaft 72 includes a central passage 79 allowing the practitioner to insert a sighting needle therein when he is centering the apparatus in relation to bone fragment 1 in the position shown schematically in FIG. 2.

Pivoting disc 80 is substantially identical to that which has just been described, the only difference lying in the positioning of the knob 85 in relation to the arm 81, and consequently the positioning of the toothed sector in relation to the connecting piece 91 for connection to the curved element 90.

Element 90 will be described in detail with reference to FIGS. 4 to 6. Connecting piece 91 is mounted to body 92 of element 90 having an arc-shaped cutout 93 over its entire height for guiding a mobile carriage 100. On the outside, body 92 has graduations 94 by means of which it is possible to measure the rotation about the axis x. A toothed sector 95 is fixed to the body 92 by way of three bosses 96.

The mobile carriage 100 includes an arc-shaped slide 101 which is intended to slide in the cutout 93 of the element 90. As can be seen in FIGS. 4 and 6, the slide 101 receives, to the left of element 90, an arc-shaped cover 102. To the right of element 90, slide 101 is continued via a body which has an opening 103 intended for the passage of toothed sector 95 meshing with a threaded rod 104 integral with the adjustment knob 105. The unthreaded parts of the screw 104 will preferably turn in bearings or bushings (not shown). Mobile carriage 100 drives a bar 107 for fastening of the pin holder flange shown schematically by the ball 5 in FIG. 2.

Before using the reducing apparatus according to the invention, care will be taken to arrange the telescopic tubes and the rotary elements in their central position, in order to permit displacements to be effected on either side of this central position. In the embodiment which is represented in the drawing, the rotations are of −20° to +20°, while the linear displacements are of 3 to 4 cm on each side of a zero point.

To put the reducing apparatus according to the invention into place, the practitioner first arranges the groups of bone pins 3 and 4 in each bone fragment 1 and 2. He then clamps these pins in the pin holders 5 and 6 which will be fixed on the fastening bars 107 and 27, respectively. At the same time he arranges the telescopic bars 20 and 30 in the positions necessitated in each specific case, by means of the connecting pieces 40 and 50. He then locks the assembly by means of the clamps 44, 54 and 59. As has already been mentioned, the practitioner arranges the reducing apparatus in the position represented in FIG. 2, arranging the bone fragment 2 on the axis x, that is to say arranging the bar 10 parallel to the bone fragment 2, while at the same time bringing the y and z axes into coincidence on the fracture site. This centering is facilitated when a sighting needle is used in central passage 79 of shaft 72, as can be seen in FIG. 3.

In order to align the bone fragments perfectly, the practitioner will then turn one of the knobs 15, 25 or 35, permitting the linear displacements of the bone fragment 2 in relation to the fragment 1, while at the same time also turning knobs 75, 85 or 105 providing for the rotational displacements. By virtue of the millimetric scales 13, 23 or 33, he will be able to measure the linear displacements, while the rotations will be indicated on the scales 68, 69 and 94, which are graduated in degrees.

The advantage of this type of manipulator is that, as each adjustment is independent, the practitioner can visualize clearly what will be the displacement effected by means of one of the three knobs for linear displacement or by means of each of the three knobs for rotational displacements. In addition, since there is a graduated scale corresponding to each movement, he will be able to displace one of the bone fragments in relation to the other by a precise value.

As has already been mentioned, the majority of the components of the angled arm 60 are radiolucent, so that the physician will be easily able to check the relative position of the bone fragments during the reduction operations.

When the bone fragments have been returned to their original position, the practitioner can replace the reducing apparatus with an external fixator, fixing the latter onto the bone pins. Depending on the specific case, it is also possible to use the reducing apparatus as an external fixator, especially if subsequent adjustments are envisaged.

While several examples of the present invention have been described, it is obvious that many changes and modifications may be made thereunto, without departing from the spirit and scope of the invention.

We claim:

1. A reducing apparatus for connecting two bone fragments on either side of an elongated bone fracture site comprising:

an adjustable circular sector having a slide device for linear displacement and a rotational coupling for angular rotations, the circular sector being divided into two curved elements which slide in relation to each other, each of the curved elements being coupled to pins for insertion in each of the bone fragments; and a radiolucent angled arm whose ends include two pivoting discs, one of the discs cooperating with a slide for linear displacements, and the other disc cooperating with said adjustable sector.

2. The reducing apparatus according to claim 1 wherein the axes of the pivoting discs is capable of being oriented on the site of the fracture, and in that the axis of the circular sector is capable of being disposed on the site of the fracture.

3. The reducing apparatus according to claim 2 wherein each pivoting disc includes a blade integral with a shaft which is intended to pivot in relation to the said disc, the blade having a toothed sector which is intended to cooperate with a screw for driving in rotation.

4. The reducing apparatus according to claim 3 wherein the pivoting discs are disposed in substantially perpendicular planes and permit a rotation of about 30° in relation to a central position.

5. A reducing apparatus for connecting two bone fragments on either side of an elongated bone fracture site comprising:

an adjustable circular sector having a slide device for linear displacement and a rotational coupling for angular rotations, the circular sector being divided into two curved elements which slide in relation to each other, each of the curved elements being coupled to pins for insertion in each of the bone fragments; and a radiolucent angled arm whose ends include two pivoting discs, one of the discs cooperating with a slide for linear displacements, and the other disc cooperating with said adjusting sector, wherein the device for linear displacements include three telescopic bars which are connected to one another by connecting pieces which are moveable in relation to said bars.

6. The reducing apparatus according to claim 5 wherein each connecting piece includes at least one opening which is of a shape corresponding to the cross-section of a bar and which opens out onto a slot and a clamp which is able to fix the connecting piece onto the corresponding bar.

7. The reducing apparatus according to claim 5 wherein each telescopic bar is made up of an inner tube equipped with a millimetric scale and an outer tube bearing arrow indications which can indicate the linear displacement of the bone fragments in response to the rotational direction of knobs integral with a screw for the relative displacement of the said tubes.

8. The reducing apparatus according to claim 7 wherein the displacement is a few centimeters on each side of a central position.

9. The reducing apparatus according to claim 5 wherein the said bars have a substantially triangular cross-section.

10. The reducing apparatus according to claim 5 wherein the bars are disposed along three orthonormal axes.

11. The reducing apparatus according to claim 5 wherein the end of one of the bars constitutes a support for the connecting piece for connection to the bone pins.

12. The reducing apparatus according to claim 1 wherein the adjustable sector is made up of a curved element which is integral with a displacement device for a mobile carriage.

13. The reducing apparatus according to claim 12 wherein the displacement device is made up of a curved toothed sector which cooperates with a screw which is integral with the mobile carriage.

14. The reducing apparatus according to claim 12 wherein the curved element has a curved opening which is intended to cooperate with a slide which is integral with the mobile carriage.

15. The reducing apparatus according to claim 14 wherein the curved element includes graduations giving the angular displacement of the mobile carriage in relation to the arc.

16. A method for putting into place the reducing apparatus according to claim 1 comprising the steps of:

placing the reducing apparatus in a position such that the angled arm is situated in a plane perpendicular to a longitudinal axis of a fractured bone;

positioning the plane of the circular sector on the site of the fracture;

situating the slide device for linear displacement on one side of the plane of the circular sector, wherein the linear displacements of the slide device are on three orthonormal axes and the rotations in relation to these same axes are effected separately and independently;

placing rotational coupling on the other side of said plane; and placing the bone fragments on either side of said plane.

* * * * *

UNITED STATES PATENT AND TRADEMARK OFFICE
CERTIFICATE OF CORRECTION

PATENT NO. : 6,001,097
DATED : December 14, 1999
INVENTOR(S) : Campopiano et al.

It is certified that error appears in the above-identified patent and that said Letters Patent is hereby corrected as shown below:

Column 3, line 57, "and" (second occurrence) should read -- are --.
Column 5, line 37, "is" should read -- are --.
Column 6, line 2, "adjusting" should read -- adjustable --.
Column 6, line 3, "include" should read -- includes --.

Signed and Sealed this

Thirtieth Day of January, 2001

Attest:

Q. TODD DICKINSON

*Attesting Officer*  *Director of Patents and Trademarks*